United States Patent [19]
Storz

[11] 3,939,840
[45] Feb. 24, 1976

[54] OPERATION ENDOSCOPE
[75] Inventor: Karl Storz, Auf dem Schildrain, Germany
[73] Assignee: Storz-Endoskop GmbH, Schaffhausen, Switzerland
[22] Filed: July 18, 1974
[21] Appl. No.: 489,775

[30] Foreign Application Priority Data
July 26, 1973 Germany............................ 7327364

[52] U.S. Cl. .......................................... 128/303.15
[51] Int. Cl.² ......................................... A61B 17/32
[58] Field of Search..... 128/303.15, 303.13, 303.14, 128/303.16, 303.17, 407–409

[56] References Cited
UNITED STATES PATENTS

| | | | |
|---|---|---|---|
| 1,952,617 | 3/1934 | Wappler | 128/303.15 |
| 2,018,335 | 10/1935 | Wappler | 128/303.15 |
| 2,888,017 | 5/1959 | Wallace | 128/303.15 |
| 3,294,085 | 12/1966 | Wallace | 128/303.15 |
| 3,850,175 | 11/1974 | Iglesias | 128/303.15 |

FOREIGN PATENTS OR APPLICATIONS

| | | | |
|---|---|---|---|
| 1,020,980 | 2/1953 | France | 128/303.14 |
| 767,414 | 7/1934 | France | 128/303.15 |
| 1,102,341 | 3/1961 | Germany | |

Primary Examiner—Robert W. Michell
Assistant Examiner—Lee S. Cohen
Attorney, Agent, or Firm—Oliver D. Olson

[57] ABSTRACT

The elongated, hollow, thin-walled metal shaft of an operation endoscope is lined internally throughout its length by a separate thin-walled sleeve of electrical insulating material, the shaft and sleeve being mounted removably on a common head independently of each other in such manner that they are separable by relative longitudinal movement in the direction by which the sleeve is retracted rearwardly relative to the shaft, thereby affording retraction and replacement of the sleeve without removing the shaft from the operation site.

3 Claims, 3 Drawing Figures

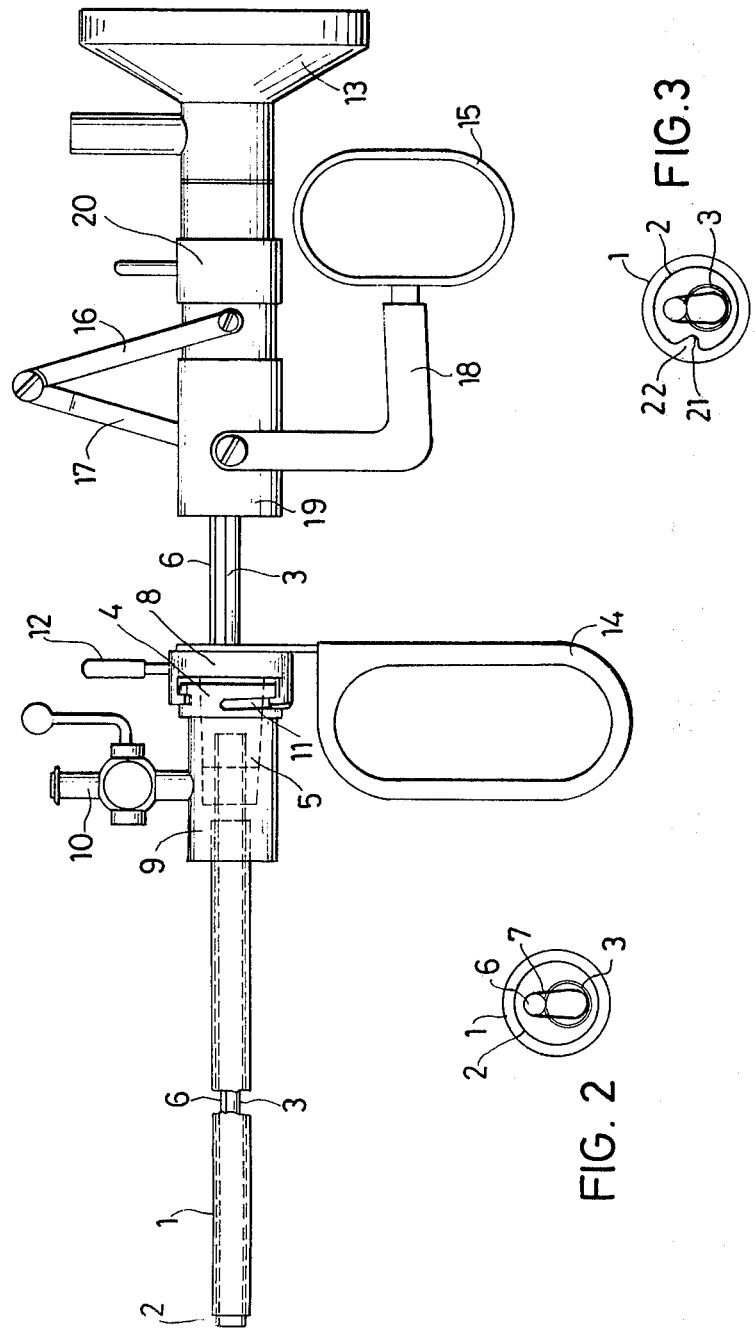

OPERATION ENDOSCOPE

This invention relates to an operation endoscope for the treatment of the urethra and bladder which, in addition to the endoscope, has a working member constructed as an electrotome with a wire electrode through which high frequency current flows during the operation, whereby the working member and the endoscope are covered by a common detachable metal endoscope shaft insulated relative to the electrotome by a member made from insulating material.

Operation endoscopes are already known wherein the member made from insulating material is constructed in one piece with the metal endoscope shaft. The endoscope shaft is made either wholly or partly of insulating material whereby the said endoscope shaft is preferably insulated over its entire length because this also ensures its insulation relative to the urethra if through an oversight the high frequency current is switched on when the working member, i.e. the electrotome with its wire electrode is located in the endoscope shaft. However, with electrical cutting, sparking occurs and the end of the endoscope shaft frequently catches fire. Thus the endoscope shaft becomes unusable. In known manner this disadvantage has been eliminated by constructing the endoscope shaft from two portions, whereby the outer portion consists of insulating material and the inner portion of metal for stabilization purposes. However, as a result of the outer and inner portions the wall thickness is considerably increased which is particularly disadvantageous when draining off or evacuating the washing liquid. In this operation it is advantageous for the internal diameter of the shaft to be as large as possible.

Finally, from German Patent No. 1,102,341 an endoscope constructed as an esophagoscope is known whose endoscope shaft contains a light source, a viewing tube and a suction device. Such suction devices were once used to remove by suction secretion in front of the viewing tube lens. However, this suction is impossible with introduction tubes with a rubber bulb. In fact the vision of the person carrying out the investigation is further imparied by the secretion. In addition, all suction devices have the disadvantages that the suction duct can become easily blocked and cannot be made permeable during the examination. To eliminate these disadvantages the esophagoscope has an introduction tube which is introduced into the endoscope shaft and has a longitudinal recess forming a duct with the inner wall of the shaft. This duct can be used to remove secretion by suction during examinations both with and without the above-indicated rubber bulb. If this duct becomes blocked it is easy to clean even during an examination by removing the introduction tube from the shaft and then reinserting it after cleaning the duct.

The problem of the invention is in particular to eliminate this disadvantage and to so improve the operation endoscope of the type described hereinbefore that a very small wall thickness of the endoscope shaft with a large internal diameter of the shaft can be obtained.

According to the invention, this problem is solved in that the portion made from insulating material is formed by a sleeve assembled with the electrotome which can be introduced into the endoscope shaft together with the electrotome.

As a result the endoscope shaft walls can be kept very thin because the sleeve has no insulation and therefore has an extremely large internal diameter. The necessary insulation relative to such an endoscope shaft is obtained by the said sleeve which is constructed completely separately from the endoscope shaft and forms a structural unit with the working member.

According to a further development of the invention, the insulating sleeve is detachably connected with the electrotome. Consequently the sleeve is replaceable. Thus, if during the operation the sleeve is damaged, it can easily be replaced by another after removing the working member. The endoscope shaft can then remain in the urethra, thereby eliminating the danger of injury resulting from reinsertion. Preferably the insulating sleeve is fitted in a corresponding mounting of the fixed head of the electrotome. In this way it is extremely easy to replace the sleeve.

Further advantages and details of the invention can be gathered from the following description of two embodiments with reference to the drawings, wherein show:

FIG. 1, a side view of the operation endoscope according to the invention;

FIG. 2, a greatly enlarged front view of the remote end of the operation endoscope;

FIG. 3, a view as in FIG. 2 of a further embodiment.

To the left of FIG. 1 is shown the endoscope shaft 1 provided at its right-hand end with a reinforcement 9 for receiving a washing pipe 10 and a bayonet catch 11, operable by a bayonet ring 8 which can be turned by means of attachment 12 in order to release the endoscope shaft 1 which can then be removed to the left.

Besides the fixed endoscope 3 with the eye piece 13 and the not shown lens at the remote end is arranged a working member by means of the axially movable operating rod 6 with wire electrode 7. This working member is a so-called electrotome because the wire electrode 7 operates with high frequency current in not shown manner of FIG. 2. Such electrotomes and their operation are already known. The operation takes place by means of the two handles 14 and 15, whereby handle 14 is fixedly connected by the head 4 of the electrotome, while handle 15 for the thumb is movable by rods 16, 17, 18. Sleeve 19 together with operating rod 6 then slides in the axial direction towards endoscope 3. The details of this operation need not be explained because they are already known. It is also possible to provide a further bayonet catch 20 in order to detach the endoscope and remove it from the endoscope sleeve 2 to the right in FIG. 1.

According to the invention, endoscope shaft 1 has in addition to the above-indicated reinforcement 9 a thin-walled metal sleeve which embraces an insulating sleeve 2 made of insulating material. This can be best gathered from FIG. 2 which also shows operating rod 6 with wire electrode 7 fixed thereto at the remote end of the endoscope 3. According to the invention, the insulating sleeve 2 forms a structural unit with the electrotome and is fitted in a corresponding mounting 5 of the fixed head 4 of the electrotome. This is shown in broken lines in FIG. 1. As can be seen, the insulating sleeve 2 is somewhat longer than endoscope shaft 1 so that it projects somewhat at the remote end to the left in FIG. 1.

In order to disassemble the operation endoscope shown in FIG. 1, the bayonet ring 8 is turned so that endoscope shaft 1 with its reinforcement 9 can be removed to the left. However, according to the invention the insulating sleeve 2 remains fitted in the head 4 of the fixed electrotome. If necessary, it can be then removed and replaced. This is extremely important because if the insulating sleeve 2 is damaged it can be easily and rapidly replaced in the indicated manner, whereby during the operation it is also possible to proceed in the reverse manner. The endoscope shaft 1 then for example remains in the urethra and after detaching the indicated bayonet catch 8, 9 the remaining equipment is removed together with the insulating sleeve 2. This avoids the danger of injury through reinsertion of the endoscope shaft 1 into the urethra or the like.

FIG. 3 shows a further preferred embodiment which differs from that according to FIGS. 1 and 2 in that the sleeve 2 is provided with a rolled-in portion 21 representing a longitudinal recess. As a result between endoscope shaft 2 and rolled-in portion 21 a cavity is formed in the longitudinal direction which can be used as an additional washing duct 22. This is often very advantageous in order to remove by suction the washing liquid supplied, for example, to the inner area of the insulating sleeve 2 by means of washing duct 22. It is also possible to remove secretion by suction.

In this case it is particularly easy to clean the washing duct 22 by removing sleeve 2 from endoscope shaft 1. After cleaning the outer duct 22 the sleeve can then be reinserted.

It is naturally necessary to provide for this additional washing duct 22 a corresponding connection on the operation endoscope according to FIG. 1, i.e. a second additional washing pipe corresponding to washing pipe 10 visible in FIG. 1. This is readily comprehensible to the skilled expert so that there is no need to show this second washing pipe.

It will be apparent to those skilled in the art that various changes may be made in the size, shape, type, number and arrangement of parts described hereinbefore, without departing from the spirit of this invention.

Having now described my invention and the manner in which it may be used, I claim:

1. An operation endoscope, comprising:
  a. an electrotome including an electrode, an elongated operating rod connected to said electrode and a head member slidably supporting the operating rod for longitudinal movement relative thereto,
  b. an elongated hollow sleeve of electrical insulating material mounted at its rearward end on the head member and extending forwardly therefrom freely around the operating rod, and
  c. an elongated hollow metal endoscope shaft freely encircling the sleeve and mounted removably at its rearward end on the head member independently of the sleeve, whereby the endoscope shaft and sleeve are separable from each other by relative longitudinal movement in the direction by which the sleeve is retracted rearwardly relative to the shaft,
  d. the sleeve extending forwardly at least to the forward end of the shaft.

2. The operation endoscope of claim 1 wherein the sleeve is connected detachably at its rearward end to the head member.

3. The operation endoscope of claim 1 wherein the sleeve is provided with a rolled-in portion in the longitudinal direction thereof which forms a washing duct with the adjacent inner surface of the separable endoscope shaft.

* * * * *